United States Patent [19]

Tolino et al.

[11] Patent Number: 4,654,702
[45] Date of Patent: Mar. 31, 1987

[54] PORTABLE AND COLLAPSIBLE PIPE CRAWLER

[75] Inventors: Ralph W. Tolino, Wilkinsburg; Edward H. Smith, Brave; Stephanie M. Havoic-Conroy, N. Huntingdon Twp., Westmoreland County, all of Pa.

[73] Assignee: Westinghouse Electric Corp., Pittsburgh, Pa.

[21] Appl. No.: 670,422

[22] Filed: Nov. 9, 1984

[51] Int. Cl.$^4$ .................. H04N 7/18; B61B 13/10
[52] U.S. Cl. ............................ 358/100; 104/138.2
[58] Field of Search .................. 358/100; 104/138 G; 138/97; 378/60

[56] References Cited

U.S. PATENT DOCUMENTS

| 3,168,908 | 2/1965 | Zurbrigen | 138/97 |
| 3,718,978 | 3/1973 | Van Koevering et al. | 104/138 G |
| 3,761,623 | 9/1973 | Hara | 358/100 |
| 3,775,612 | 11/1973 | Foster | 378/60 |
| 3,915,197 | 10/1975 | Piccirilli | 138/97 |
| 3,979,941 | 9/1976 | Auxer | 104/138 G |
| 3,987,666 | 10/1976 | Blanc | 358/100 |
| 4,006,359 | 2/1977 | Sullins et al. | 104/138 G |
| 4,034,679 | 7/1977 | Gaither et al. | 104/138 G |
| 4,057,081 | 11/1977 | Jones | 138/97 |
| 4,112,850 | 9/1978 | Sigel-Gfeller | 104/138 G |
| 4,177,734 | 12/1979 | Rhoden | 104/138 G |
| 4,194,218 | 3/1980 | Hasegawa | 358/100 |
| 4,244,296 | 1/1981 | Vertut | 104/138 G |
| 4,272,781 | 6/1981 | Taguchi | 358/100 |
| 4,369,713 | 1/1983 | Richardson | 104/138 G |
| 4,460,920 | 7/1984 | Weber | 358/100 |
| 4,526,106 | 7/1985 | Okada | 378/60 |
| 4,537,136 | 8/1985 | Douglas | 378/60 |

FOREIGN PATENT DOCUMENTS 2640055  9/1978  Fed. Rep. of Germany .

Primary Examiner—Howard W. Britton
Attorney, Agent, or Firm—L. A. DePaul

[57] ABSTRACT

A light-weight, portable, pipe crawler vehicle includes a four-wheeled chassis, with the sets of wheels along the opposite sides of the chassis being respectively driven by two hydraulic motors. A foldable mast is removably pivotally mounted on the chassis and carries a pneumatic cylinder which, when the mast is in its erected position, forces bearing wheels against the opposite side of the pipe to force the chassis wheels into firm frictional engagement with the pipe so that it can traverse vertical pipe sections while remaining under control. The dimensions of the vehicle are such that when the mast is folded the vehicle will fit through a 16"-diameter manway of a nuclear steam generator vessel. The chassis also carries a three-axis remote manipulator and one or two remotely-controlled video cameras. A position indicator including a star wheel and proximity sensor is disposed for rolling engagement with the pipe to sense distance travelled.

20 Claims, 7 Drawing Figures

PORTABLE AND COLLAPSIBLE PIPE CRAWLER

BACKGROUND OF THE INVENTION

1. Field of Invention

The present invention relates to apparatus for the inspection and maintenance of nuclear steam generator equipment. The invention has particular application to the inspection and maintenance of pipes or other tubular passages, such as the primary loop conduit of a nuclear steam generator.

2. Description of the Prior Art

Direct on-site inspection of nuclear steam generating facilities by inspection personnel is limited because of the danger of man-rem exposure. Thus, the use of remotely-controlled mechanical inspection apparatus is necessary. A number of different types of self-propelled pipe crawler vehicles have been provided in the prior art for traversing the interior of pipes or other tubular conduits for inspection or maintenance purposes, most of these devices having been provided for use by pipeline companies. Some of these vehicles are intended for carrying of operating or inspection personnel, but others are remotely-controlled.

However, the prior pipe crawler vehicles which are intended for use in large-diameter pipes, are designed for use where there is direct access to one end of the pipe. They are not capable of passing through openings having a diameter substantially less than the diameter of the pipe. Thus, such vehicles would not be suitable for use in a nuclear steam vessel, wherein the only access to the primary loop conduit is through a much smaller-diameter manway. Furthermore, such prior devices are generally quite heavy and cumbersome and cannot be handled by one person.

A pipe crawling vehicle has been provided specifically for use in nuclear steam generator vessels, such a device being illustrated in U.S. Pat. No. 4,244,296. But that device is rather complex, including a plurality of pivotally movable arms, each independently driven, necessitating a plurality of drive mechanisms. Furthermore, the vehicle is quite heavy and cumbersome, necessitating the use of a special loading apparatus for hoisting the device into the nuclear steam generator vessel. Finally, the vehicle is of limited utility. It has only two support wheels, mounted fore and aft and, therefore, the pivoting arms must be utilized to maintain the stability of the vehicle in the tube. Accordingly, the device is usable only in a pipe or other confined space wherein there is a surface for the arms to bear against.

SUMMARY OF THE INVENTION

It is a general object of the present invention to provide an improved pipe crawler vehicle which avoids the disadvantages of prior devices while affording additional structural and operating advantages.

An important object of the invention is the provision of a pipe crawler vehicle which is uniquely adapted for use in the inspection of nuclear steam generator installations.

In connection with the foregoing object, it is another object of this invention to provide a pipe crawler vehicle which is relatively light-weight and portable so that it can be handled by a single person.

In connection with the foregoing objects, it is another object of the invention to provide a vehicle of the type set forth which is both self-propelled and remotely controlled.

Yet another object of the invention is the provision of a vehicle of the type set forth which can easily traverse curved and vertical portions of a pipe, and yet which is foldable so as to permit access through an opening substantially smaller than the pipe diameter.

Another object of the invention is the provision of a vehicle of the type set forth which is capable of use for applications outside a pipe.

Another object of the invention is the provision of a vehicle of the type set forth which can operate effectively under water.

Yet another object of the invention is the provision of a vehicle of the type set forth which includes accurate position indicating means to facilitate remote control of the device.

These and other objects of the invention are attained by providing a portable self-propelled vehicle for movement along the interior surface of a pipe and receivable into the pipe through an access opening having a predetermined diameter substantially less than the diameter of the pipe, the vehicle comprising: a carriage having a maximum lateral dimension less than the predetermined diameter, the carriage including a chassis, a plurality of wheels rotatably carried by the chassis and adapted for rolling engagement with the interior surface of the pipe, and motive means carried by the chassis for rotatably driving the wheels; a mast mounted on the carriage for pivotal movement between a folded condition extending generally parallel to the chassis and longitudinally thereof for passage through the access opening and an erected condition extending generally perpendicular to the chassis; fluid-actuated drive means carried by the mast; and bearing means coupled to the drive means, the drive means being operable for urging said bearing means into frictional rolling engagement with the interior surface of the pipe opposite the portion thereof engaged by said wheels when said mast is in the erected condition thereof positively to hold the wheels in frictional driving engagement with the pipe regardless of the orientation of the chassis.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 6 is a further enlarged, fragmentary view of the position indicating mechanism of the crawler vehicle FIG. 2; and FIG. 7 is a fragmentary view in vertical section taken along the line 7—7 in FIG. 6.

DESCRIPTION OF THE PREFERRED EMBODIMENT

Figure 1:
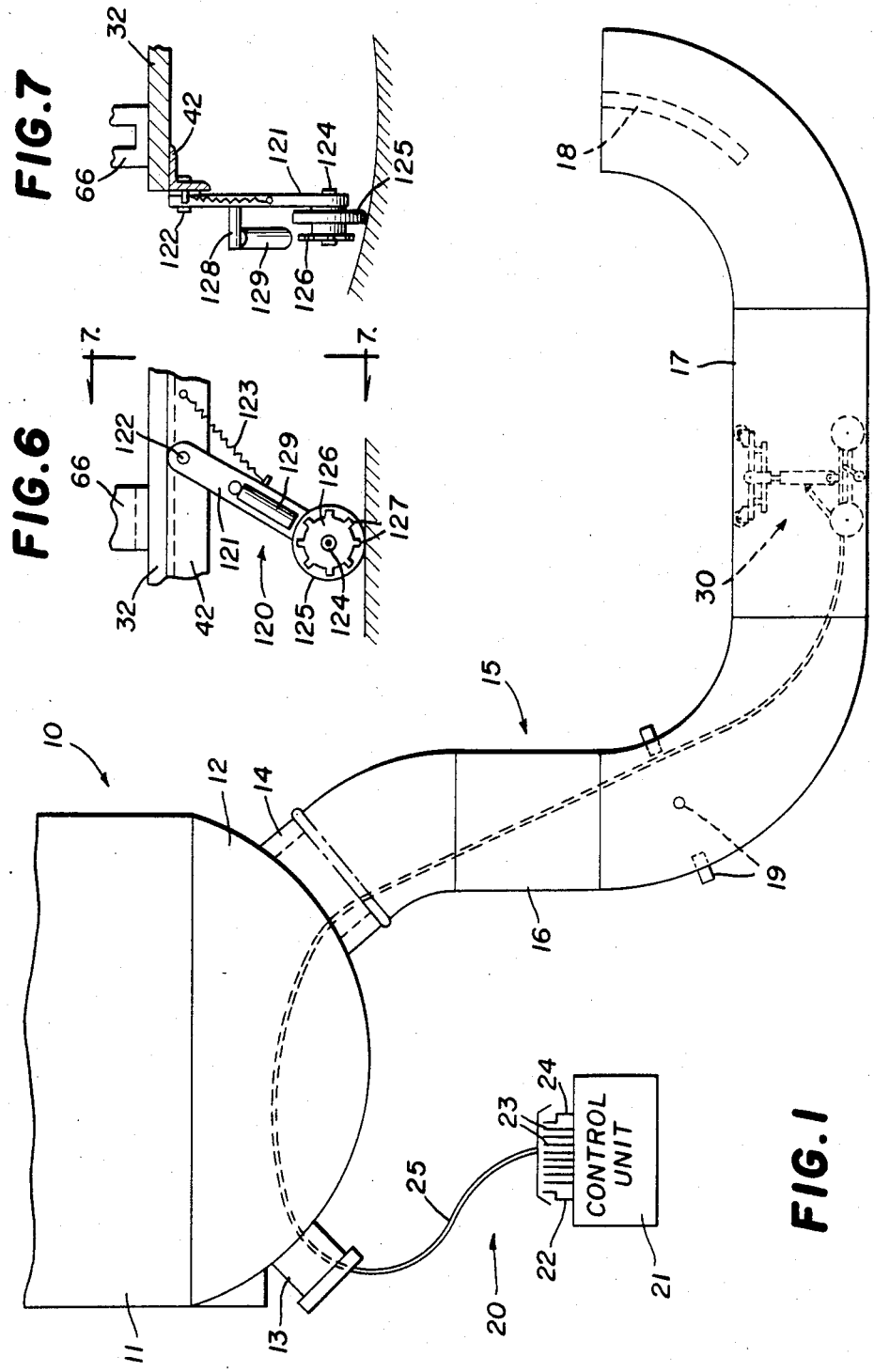
FIG. 1 is a fragmentary side elevational view of the lower end of a nuclear steam generator vessel and associated primary loop conduit, illustrating use of the pipe crawler vehicle of the present invention for inspection of the conduit.

Referring to FIG. 1, there is illustrated a portion of a nuclear steam generator vessel, generally designated by the numeral 10, which includes a cylindrical side wall 11 closed at the lower end thereof by a part-spherical bottom wall 12. The details of construction and operation of the nuclear steam generator vessel 10 form no part of the present invention, but simply provide an environment in which the present invention may operate. Accordingly, only so much of the nuclear steam generator vessel 10 as is necessary for an understanding of the present invention is disclosed herein. However, the nuclear steam generator vessel 10 is of the type disclosed in U.S. Pat. No. 4,276,856, and reference to that patent may be had for further details of construction and operation.

The lower end of the cylindrical wall 11 is closed by a circular tube sheet (not shown) which cooperates with the bottom wall 12 to define a plenum which is divided by a partition (not shown) into inlet and outlet chambers. Access to the plenum is provided by a cylindrical manway 13. Also communicating respectively with the two chambers of the plenum are two nozzles 14 (one shown), each communicating with a portion of a primary loop conduit 15 which extends to an associated nuclear reactor (not shown) for circulating reactor coolant between the nuclear reactor and the steam generator vessel 10. This coolant, which is typically water, is circulated through heat-exchange tubes (not shown) in the steam generator vessel 10 disposed in heat-exchange relationship with a secondary feedwater for converting it to steam, all in a known manner. The reactor coolant or primary water is radioactive, as are the primary loop conduits 15 and the plenum of the nuclear steam generator vessel 10. Accordingly, man-rem exposure severely limits the access of personnel to these parts of the system and effectively prevents direct inspection and maintenance by operating personnel.

Inspection of the primary loop conduit 15 is further complicated by the construction thereof. The primary loop conduit 15 has an inner surface 15a (see FIG. 3) which has a diameter substantially greater than that of the manway 13, indicated by the circle 13a. Specifically, the diameter of the surface 15a may be 27 to 30 inches, while that of the manway 13 is typically 15 or 16 inches. Furthermore, the primary loop conduit 15 includes vertical portions 16, which may include vertical drops of 8 to 10 feet, as well as horizontal portions 17 and one or more bends or curves. Typically, the primary loop conduit 15 may include a flow splitter 18 (FIG. 1) therein adjacent to the associated nuclear reactor, which splitter is subject to cracking and must be inspected. But to get to the flow splitter 18, inspection apparatus must pass a plurality of radially inwardly extending temperature sensors 19 (FIG. 3), such as resistive temperature sensors, or other types of instrumentation which project into the flow path.

To overcome all of these difficulties, the present invention provides a transport system, generally designated by the numeral 20, which includes a remote control unit 21 which may be disposed at a distance from the nuclear steam generator vessel 10. The control unit 21 is connected to associated sources of pressurized hydraulic and pneumatic fluids as well as an electric power source (not shown) and includes suitable control valves, which are in turn coupled to a plurality of hydraulic lines 22 and pneumatic lines 23 as well as an electrical cable 24. The lines 22 and 23 and the cable 24 are preferably all bound together in a cable bundle 25, the far end of which is coupled to a crawler vehicle 30 designed for passage through the primary loop conduit 15.

Referring now in particular to FIGS. 2–7 of the drawings, the crawler vehicle 30 includes a carriage, generally designated by the numeral 31, having a mast assembly 60 mounted thereon. The carriage 31 includes a flat, generally rectangular chassis platform 32 supported on four wheels including front wheels 33 and 34 and rear wheels 35 and 36, respectively fixedly secured to four stub axles 37, as by nuts 38. The wheels 33–36 are arranged so that the axles 37 are substantially parallel to the platform 32, the front axles 37 being coaxial and the rear axles 37 being coaxial, and with the front wheels 33 and 34 being respectively aligned with the rear wheels 35 and 36 substantially parallel to the longitudinal axis of the platform 32. Each axle 37 is journalled in an outboard bearing 39 and an inboard bearing 40 fixedly secured to and depending from the platform 32.

The platform 32 and the wheels 33–36 may all be formed of metal, the wheels 33–36 preferably being provided with a plurality of lightening holes 41. Similarly, the platform 32 may be provided with lightening apertures (not shown) to reduce the overall weight of the vehicle 30. Two angle beams 42 are fixedly secured to the underside of the platform 32, respectively along the opposite side edges thereof, and extend between the front and rear ones of the outboard bearings 39. Each of the wheels 33–36 has a narrow cylindrical surface 43 at the outer edge thereof and a part-spherical central surface 44, the surfaces 43 and 44 being joined by a frustoconical surface 45 bevelled at an angle to engage substantially flush against the inner surface 15a of the primary loop conduit 15 (see FIG. 3). Preferably, each of the wheels 33–36 is provided with a tread 46 (FIG. 5) along the frustoconical surface 45 thereof, which tread may be formed of any suitable frictional material such as urethane.

The carriage 31 also includes a pair of drive assemblies 50 which are substantially the same in construction and operation, wherefore only one will be described in detail. One of the drive assemblies 50 is connected for driving in tandem the wheels 33 and 35 along the left-hand side of the carriage 31 and the other of the drive assemblies 50 is connected for driving in tandem the wheels 34 and 36 along the right-hand side of the carriage 31. Each drive assembly 50 includes a hydraulic motor 51 fixedly secured to the underside of the platform 32 by suitable means. The motor 51 has an output shaft 52 disposed parallel to the platform 32 and perpendicular to the longitudinal axis thereof. The motors 51 are respectively disposed adjacent to the opposite ends of the carriage 31, just longitudinally inwardly of the bearings 40, with each output shaft 52 projecting toward the pair of wheels to be driven thereby.

Fixedly secured to the output shaft 52 is a spur gear 53 disposed in meshing engagement with a gear 54 which is fixedly mounted on the adjacent one of the axles 37. That axle 37 also carries a sprocket 55 which engages an endless chain 56, which in turn engages another sprocket 57 mounted on the other axle 37 along the same side of the platform 32. Also engaged with the chain 56 is a tensioning sprocket 58 which is carried adjacent to the distal end of an elongated pivot bracket 59 which is mounted for pivotal movement on the adjacent one of the angle beams 42 to control the tension in the chain 56.

Each motor 51 is coupled by suitable fittings (not shown) to an associated pair of the hydraulic lines 22 for respectively controlling forward and reverse rotation of the motor 51. However, the hydraulic connections have not been shown in FIGS. 2-7 to avoid cluttering of the drawings and obscuring of the mechanical structure. The direction of motion of the carriage 31 can be controlled by selective control of the direction of the rotation of the two motors 51. Thus, for moving the carriage 31 forward, both motors 51 would be operated in the forward direction, and to move the carriage 31 backward, both motors 51 would be operated in the reverse direction. If only one of the motors 51 is operated the carriage will turn from either a forward or rearward direction, depending upon the direction of rotation of the motor. It will be appreciated that the radius of a turn can be shortened by operating one of the motors 51 in the forward direction and the other in the reverse direction.

Figure 2:
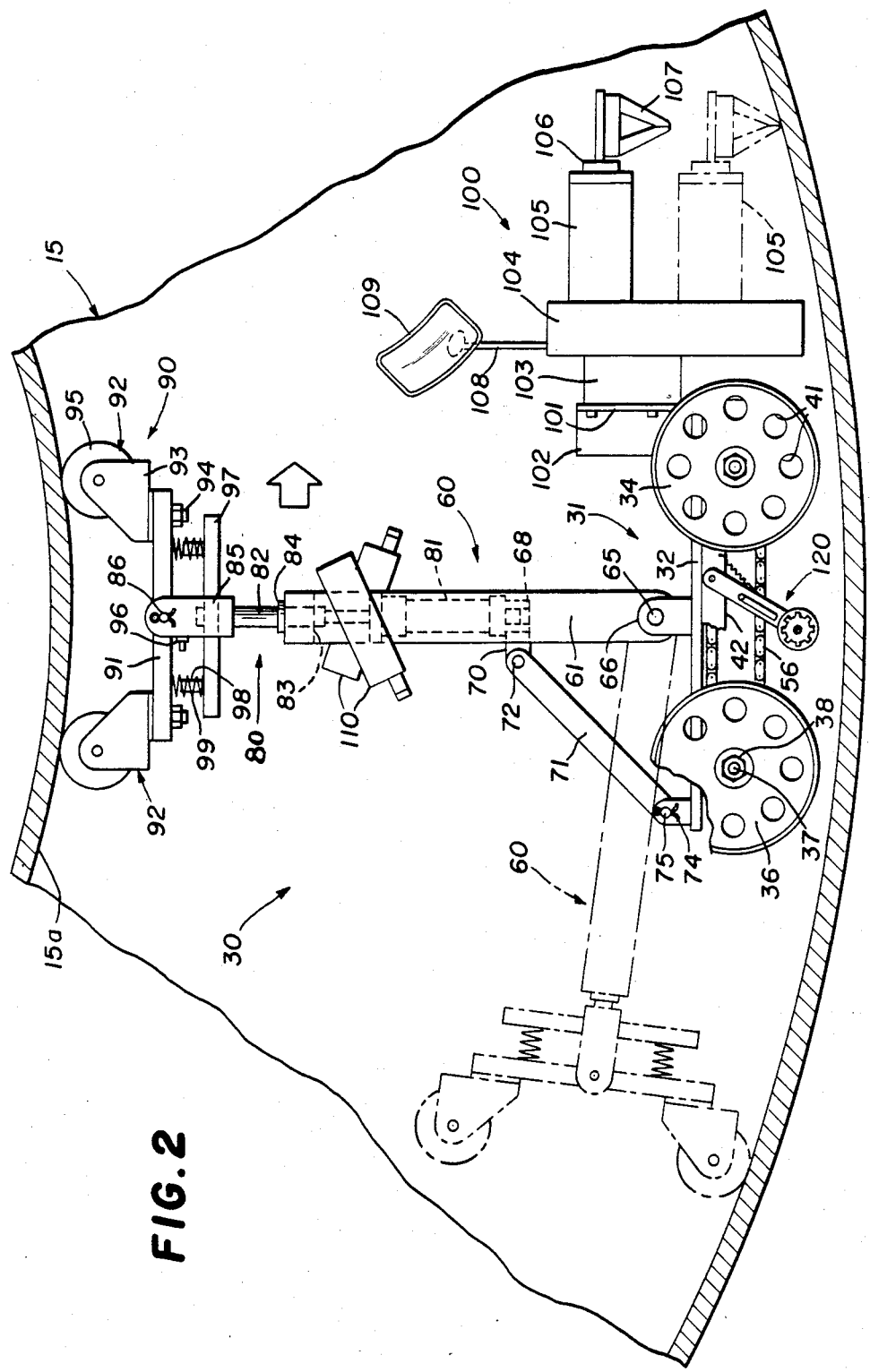
FIG. 2 is an enlarged, fragmentary view in vertical section through a curved portion of the conduit of FIG. 1, illustrating the pipe crawler vehicle of the present invention in elevation, and indicating movement of several of the parts thereof.
Figure 3:
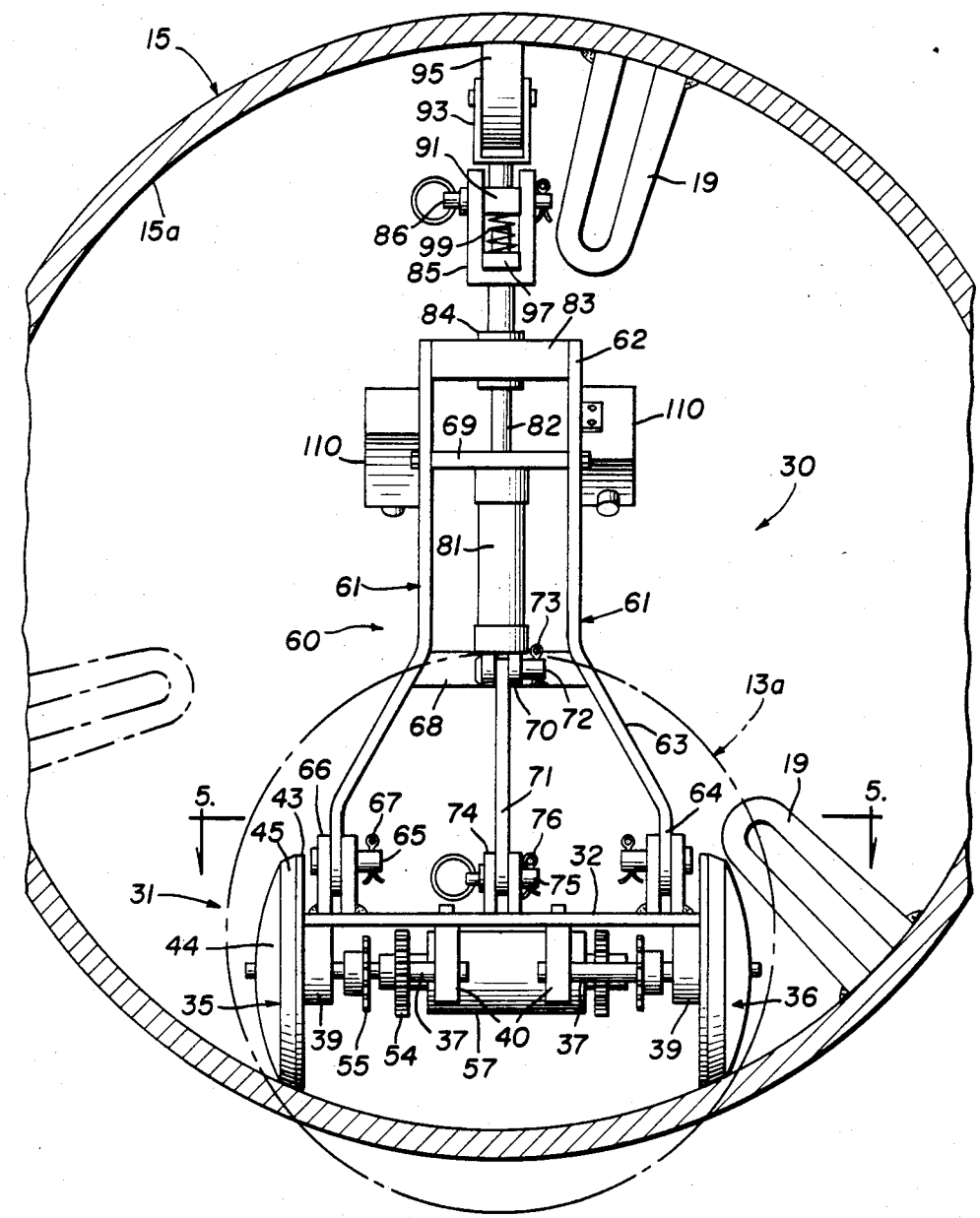
FIG. 3 is a still further enlarged view in vertical section through the primary loop conduit of FIG. 1, illustrating the pipe crawler vehicle in end elevation.
Figure 4:
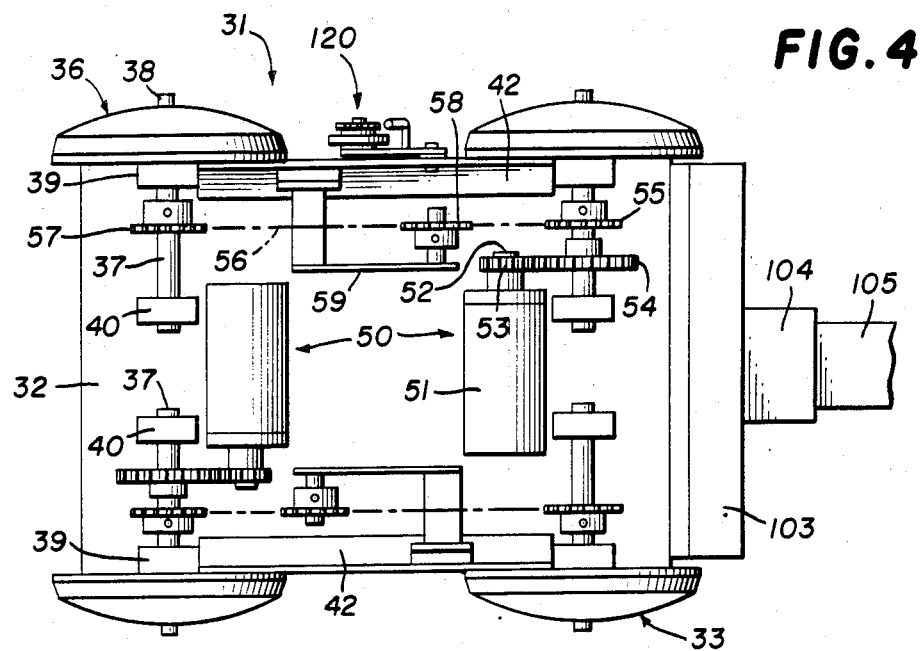
FIG. 4 is a fragmentary bottom plan view of the pipe crawler vehicle of FIG. 3, rotated 90° clockwise.
Figure 5:
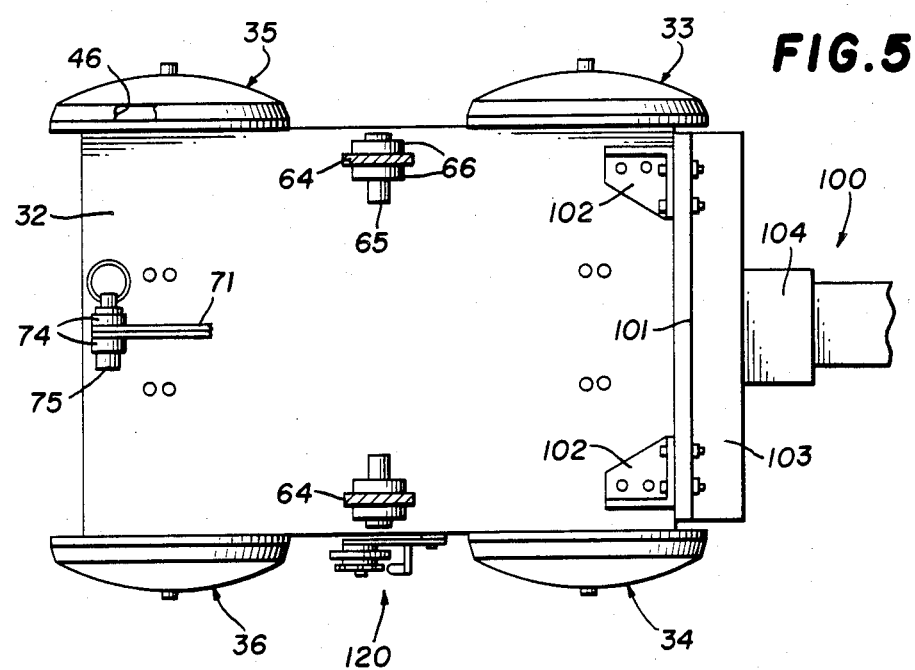
FIG. 5 is a fragmentary view in horizontal section taken along the line 5—5 in FIG. 3, and rotated 90° clockwise.

Referring in particular to FIGS. 2 and 3, the mast assembly 60 includes a pair of laterally spaced-apart legs 61, each in the form of a flat bar, and each having an upper portion 62 extending parallel to the longitudinal midplane of the carriage 31, a laterally outwardly inclined portion 63 and a lower portion 64 disposed substantially parallel to the upper portion 62. The lower portions 64 are respectively received between pairs of pivot blocks 66 and are pivotally secured thereto, as by headed pivot pins 65, retained in place by cotter pins 67. The pivot blocks 66 are respectively fixedly secured to the upper surface of the platform 32, as by welding, respectively adjacent to the opposite sides thereof and substantially midway between the front and rear ends thereof.

The upper portions 62 of the legs 61 are arranged parallel to each other and in alignment laterally of the carriage 31, being interconnected by vertically spaced-apart lower and upper cross bars 68 and 69. Fixedly secured to the lower cross bar 68 intermediate its end and projecting outwardly therefrom substantially parallel to the platform 32 are a pair of clevis lugs 70, which receive therebetween the upper end of an elongated brace arm 71, being coupled thereto by a pivot pin 72 retained in place by a cotter pin 73. The opposite end of the brace arm 71 is received between a pair of clevis lugs 74 fixedly secured to the platform 32 adjacent to the rear end thereof and midway between the opposite sides thereof, being pivotally connected thereto by a pivot pin 75, retained in place by a cotter pin 76.

In operation, the mast assembly 60 is pivotally movable between an erected condition, illustrated in solid line in FIGS. 2 and 3, wherein the legs 61 extend vertically upwardly from the platform 32, and a folded condition, illustrated in broken line in FIG. 2, extending rearwardly generally parallel to the platform 32. When the mast assembly 60 is in its erected condition, it is locked in place by the brace arm 71. In order to permit movement of the mast assembly 60 in its folded condition, the brace arm 71 is disconnected from the clevis lugs 74 by removal of the pivot pin 75, the brace arm 71 being folded upwardly along the rear side of the mast assembly 60. It will, of course, be appreciated that the mast assembly 60 can be disconnected entirely from the carriage 31 by removal of the pivot pins 65.

The mast assembly 60 carries a pressure assembly, generally designated by the numeral 80, which includes a double-acting pneumatic cylinder 81 fixedly secured between the lower and upper cross bars 68 and 69 and having a piston rod 82. The piston rod 82 projects outwardly through a corresponding aperture in the upper cross bar 69 and through a bearing 84 in a top beam 83 which interconnects the upper portions 62 of the legs 61 at the distal ends thereof. Fixedly secured to the distal end of the piston rod 82 is a clevis bracket 85, the legs of which are spanned by a pivot pin 86 for pivotally mounting a guide assembly 90.

More particularly, the guide assembly 90 includes an elongated bar 91 which extends between the legs of the clevis bracket 85 and receives the pivot pin 86 therethrough intermediate the ends thereof. Preferably, the clevis bracket 85 is secured in place so that the bar 91 extends generally along the longitudinal midplane of the carriage 31. Respectively mounted on the bar 91 adjacent the opposite ends thereof are two casters 92, each including a bracket 93 mounted on a pin 94, and a rotatably mounted wheel 95. A retainer 96 is removably mountable on the clevis bracket 85 for retaining the guide assembly 90 in an operating condition, illustrated in solid line in FIGS. 2 and 3, with the bar 91 disposed substantially parallel to the platform 32. In this condition, the wheels 95 are respectively disposed forwardly and rearwardly of the carriage 31 for rolling engagement with the inner surface 15a of the primary loop conduit 15, as will be explained more fully below. An elongated bar 97 extends between the legs of the clevis bracket 85 beneath the bar 91 and parallel thereto, the bar 97 being somewhat shorter than the bar 91 and fixedly secured, as by a threaded fastener, to the bight portion of the clevis bracket 85. Respectively fixed, as by welding, to the upper surface of the bar 97 adjacent to the opposite ends thereof are two cylindrical retainers 98, which are respectively received in two helical compression springs 99. The springs 99 bear against the underside of the bar 91, the cylindrical retainers 98 terminating a predetermined below the bar 91. The springs 99 resiliently bias the bar 91 to a horizontal operating position illustrated in the drawings, the upper ends of the retaining cylinders 98 serving to limit the pivotal movement of the bar 91 from that operating position.

It will be appreciated that the pneumatic lines 23 are respectively connected by suitable fittings (not shown) to the upper and lower ends of the cylinder 81 for extending and retracting the piston rod 82. Alternatively, the piston rod 82 could be spring-biased to its retracted condition and the cylinder 81 could be a single-acting cylinder.

Also mounted on the carriage 31 at the front end thereof is a manipulator assembly 100. More specifically, a rectangular mounting plate 101 is fixedly secured to the front edge of the platform 32 and extends upwardly therefrom substantially perpendicular thereto, the plate 101 being secured and braced in place by corner brackets 102. Mounted on the plate 101 and projecting forwardly therefrom is a horizontal track beam 103 on which is mounted a vertical track beam 104, which is adapted to move back and forth longitudinally of the track beam 103 and laterally of the carriage 31. Mounted on the vertical track beam 104 and projecting forwardly therefrom is a longitudinal beam 105, adapted to move vertically along the track beam 104. The longitudinal beam 105 includes a telescoping section 106 which moves in and out forwardly and rearwardly with respect to the carriage 31 and carries at its distal end a gripper mechanism 107. The manipulator assembly 100 is of known construction and may be of the type sold by Mack Corporation under the designation Polymorphic Series 2. It will be appreciated that the manipulator assembly 100 provides movement along three mutually perpendicular axes, the movement being effected by pneumatic cylinders (not shown).

Mounted on top of the vertical track beam 104 is an upstanding support post 108 which carries a convex rearview mirror 109. Mounted on the mast assembly 60 is at least one video camera 110 mounted so as to be directed toward the manipulator assembly 100 to view the operation thereof and the path ahead of the carriage 31. The vertical track beam 104 may be moved horizontally along the horizontal track beam 103 to move the rearview mirror 109 into the field of view of the video camera 110 for viewing the area behind the carriage 31. Alternatively, a second rearwardly-directed video camera 110 may be provided on the mast assembly 60. Both the video cameras 110 are connected by the cable 24 to the control unit 21, which may include a video monitor. The cable 24 may also include conductors for transmitting electricity to one or more light sources (not shown) which may be mounted on the mast assembly 60 for illuminating the field of view of the video cameras 110.

Referring in particular to FIGS. 2, 6 and 7, the carriage 31 also includes a position and distance indicator 120. The indicator 120 includes an elongated arm 121 pivoted at one end thereof, as by a pivot pin 122, to the angle beam 42 along one side of the carriage 31, between the front and rear wheels thereof. A bias spring 123 interconnects the angle beam 42 and a point intermediate the ends of the arm 121 to bias it into a downward use position, illustrated in the drawings. Rotatably carried by the arm 121 adjacent to its distal end, and projecting laterally outwardly therefrom substantially normal thereto is a shaft 124 which has fixedly secured thereto a roller 125 disposed for rolling engagement with the inner surface 15a of the primary loop conduit 15. Also fixedly mounted on the shaft 124 for rotation therewith is a star wheel 126 having a plurality of equiangularly spaced-apart and radially outwardly extending lugs 127 thereon (FIG. 6). The star wheel 126 is dimensioned so that the lugs 127 clear the inner surface 15a of the primary loop conduit 15 when the roller 125 is in contact therewith. Projecting laterally outwardly from the arm 121 intermediate its ends is a short bracket 128 which carries a magnetic proximity sensor 129 disposed so that the lugs 127 pass in close proximity thereto during rotation of the shaft 124.

In operation, as the carriage 31 rolls along the inner surface 15a of the primary loop conduit 15 or other support surface, the roller 125 engages that surface for frictional rotation thereof. This effects a corresponding rotation of the star wheel 126. Each time a lug 127 passes the proximity sensor 129 it produces an electrical signal pulse. The indicator 120 is calibrated so that the angular distance between the lugs 127 corresponds to a predetermined linear distance travelled by the carriage 31. Thus, the total distance travelled from a known reference starting point can be determined by counting the pulses produced by the indicator 120 and noting the direction of movement of the carriage 31. The indicator 120 is connected to the control unit 21 via the cable 24. Preferably, the control unit 21 includes circuitry responsive to the direction of rotation of the motors 51 and the pulses from the indicator 120 for maintaining a continuous and accurate plot of the distance and direction travelled by the carriage 31 and, by comparison to the known starting reference, the position of the crawler vehicle 30.

The operation of the transport system 20 and the crawler vehicle 30 thereof will now be described. It is a fundamental feature of the present invention that the crawler vehicle 30 is relatively light-weight, so that it can conveniently be handled by a single maintenance person. Preferably, the crawler vehicle 30 weighs 60 pounds or less so that it can be carried into the plenum of the nuclear steam generator vessel 10 and erected at the mouth of the primary loop conduit 15 by one person in less than two minutes, so as to minimize man-rem exposure. It is another fundamental aspect of the present invention that the crawler vehicle 30, particularly in the folded condition of the mast assembly 60, is compact so that it can freely pass through the manway 13, which is typically about 16" in diameter. Thus, the overall maximum width of the carriage 31 is less than 16" and the overall height of the vehicle 30, when the mast assembly 60 is in its folded condition, is also less than the diameter of the manway 13, which is indicated by the broken circle 13a in FIG. 3. In this regard, it will be appreciated that no part of the mast assembly 60 or the manipulator assembly 100 extends laterally beyond the lateral boundaries of the carriage 31.

When the crawler vehicle 30 has been inserted into the plenum of the steam generator vessel 10, it is erected by moving the mast assembly 60 to its erected condition and locking the brace arm 71 in place, and by attaching the retainer 96 to hold the guide assembly 90 in its use position. The crawler vehicle 30 is then manually inserted into the mouth of the primary loop conduit 15, with the wheels 33–36 of the carriage 31 in rolling engagement with the inner surface 15a, as indicated in FIG. 3. The cylinder 81 is the actuated to drive the wheels 95 up into frictional rolling engagement with the inner surface 15a of the primary loop conduit 15 diametrically opposite the portion of the surface engaged by the wheels 33–36. The pushing of the pressure assembly 80 against the primary loop conduit 15 serves to urge the wheels 33–36 into firm frictional engagement with the inner surface 15a, the force exerted by the cylinder 81 being sufficient to securely hold the crawler vehicle 30 in position in the vertical portion 16 of the primary loop conduit 15 against the force of gravity, so that linear movement of the carriage 31 is effected only in response to actuation of the drive assemblies 50. The maintenance person then exits the nuclear steam generator vessel 10 and control of the crawler vehicle 30 is effected solely by the remote control unit 21.

As the vehicle 30 moves along the primary loop conduit 15, the path ahead and behind can be viewed with the video camera or cameras 110 and the rearview mirror 109. If desired, the orientation of the cameras 110 may also be remotely controllable. In this way, the interior of the conduit 15 is remotely inspected. In the event that debris or other articles are detected in the conduit 15 which must be removed, the manipulator assembly 100 can be used for this purpose. It will be appreciated that, if desired, other types of instrumentation can also be carried by the crawler vehicle 30.

Referring to FIG. 3, it can be seen that the size and unique shape of the crawler vehicle 30 is such that it can clear the temperature sensors 19 and thus roll unobstructed along the entire length of the primary loop conduit 15. The hydraulic and pneumatic drives for the movable elements facilitates operation of the crawler vehicle 30 to be operated underwater so that it can be used whether or not the primary loop conduit 15 is filled. The cylinder 81 permits a substantial travel of the guide assembly 90 so that the crawler vehicle 30 is adaptable to variations in the diameter of the primary loop conduit 15. Similarly, the compressibility of the pneumatic fluid and the limited pivotal movement of the guide assembly 90 accommodated by the springs 99 permit the vehicle 30 to resiliently roll over minor bumps or discontinuities along the inner surface 15a.

While hydraulic motors 51 and a pneumatic cylinder 81 have been disclosed, it will be appreciated that other types of power sources could be used. Thus, the cylinder 81 could also be hydraulic and the motors 51 could be air motors or electric motors. However, hydraulic and pneumatic power sources are preferred in the case of submersible operation.

It will be understood that in the event of malfunction of the crawler vehicle 30, it can be retrieved from the conduit 15 and the nuclear steam generator vessel 10 by pulling on the cable bundle 25 without having to send personnel into the conduit 15.

While the crawler vehicle 30 has been disclosed particularly for use in inspecting a conduit such as the primary loop conduit 15, it will be appreciated that it could be utilized for other servicing and inspection duties. Thus, for example, it could be utilized in a flooded nuclear reactor cavity to run beneath and inspect the reactor internals while they are mounted in a stand, such as for inspection of the split pins.

In a constructional model of the present invention, the platform 32 and the wheels 33–36 and the structural members of the mast assembly 60 may be formed of stainless steel, or other suitable material which can withstand the environment of the primary loop conduit 15. This environment includes radiation fields of up to 50 R/HR., water containing up to 2,500 PPM boric acid and a temperature of up to 160° F. The lugs 127 of the star wheel 126 are formed of a magnetically permeable material.

From the foregoing, it can be seen that there has been provided an improved transport system including a crawler vehicle which is portable, compact and self-propelled and which is capable of operation in vertical and horizontal conduit sections while remaining under full remote control, and which is capable of operation in the hostile environment of a nuclear steam generator vessel.

We claim as our invention:

1. A portable self-propelled vehicle for movement along the interior surface of a pipe and receivable into the pipe through an access opening having a predetermined diameter substantially less than the diameter of the pipe, said vehicle comprising: a carriage having a maximum lateral dimension less than said predetermined diameter, said carriage including a chassis, a plurality of wheels rotatably carried by said chassis and adapted for rolling engagement with the interior surface of the pipe, and motive means carried by said chassis for rotatably driving said wheels; a mast mounted on said carriage for pivotal movement between a folded condition extending generally parallel to said chassis and longitudinally thereof for passage through the access opening and an erected condition extending generally perpendicular to said chassis; fluid-actuated drive means carried by said mast; and bearing means coupled to said drive means; said drive means being operable for urging said bearing means into frictional rolling engagement with the interior surface of the pipe opposite the portion thereof engaged by said wheels when said mast is in the erected condition thereof positively to hold said wheels in frictional driving engagement with the pipe regardless of the orientation of said chassis.

2. The vehicle of claim 1, wherein said carriage includes four wheels.

3. The vehicle of claim 1, wherein said motive means includes a hydraulic motor.

4. The vehicle of claim 1, wherein said mast is removably mounted on said carriage.

5. The vehicle of claim 1, wherein said mast includes a pair of legs pivotally mounted on said carriage, and brace means for locking said mast in the erected condition thereof.

6. The vehicle of claim 1, wherein said drive means includes a pneumatic cylinder.

7. The vehicle of claim 1, wherein said bearing means includes a pair of bearing wheels.

8. The vehicle of claim 1, and further including camera means carried by said mast, and remote control and monitor means coupled to said camera means for controlling the operation thereof in viewing the interior of the pipe.

9. The vehicle of claim 8, and further including manipulator means mounted on said carriage for movement about three mutually perpendicular axes, said remote control means being coupled to said manipulator means for control thereof.

10. The vehicle of claim 9, and further including mirror means carried by said manipulator means for movement into and out of the line of sight of said camera means for permitting viewing in a direction rearwardly of said camera means.

11. A portable self-propelled vehicle for movement along the interior surface of a pipe, said vehicle comprising: a chassis, a pair of laterally spaced-apart front wheels and a pair of laterally spaced-apart rear wheels carried by said chassis respectively adjacent to the front and rear ends thereof and adapted for rolling engagement with the interior surface of the pipe, first motive means carried by said chassis for rotatably driving in tandem the righthand wheels of said pairs of wheels, second motive means carried by said chassis for rotatably driving in tandem the left-hand wheels of said pairs of wheels, and remote control means coupled to said first and second motive means for selectively controlling the operation thereof independently of each other.

12. The vehicle of claim 11, wherein each of said wheels includes a resilient frictional tread disposed for engagement with the interior surface of the pipe.

13. The vehicle of claim 11, wherein each of said motive means includes a hydraulic motor.

14. The vehicle of claim 13, wherein each of said motive means includes a chain and sprocket assembly interconnecting the associated two of said wheels, and gear means coupling the associated one of said hydraulic motors to said chain and sprocket assembly.

15. The vehicle of claim 11, and further including camera means carried by said chassis for viewing the interior of the pipe.

16. A portable self-propelled vehicle for movement along the interior surface of a pipe, said vehicle comprising: a chassis, a pair of laterally spaced-apart front wheels and a pair of laterally spaced-apart rear wheels carried by said chassis respectively adjacent to the front and rear ends thereof and adapted for rolling engagement with the interior surface of the pipe, first motive means carried by said chassis for rotatably driving in tandem the righthand wheels of said pairs of wheels, second motive means carried by said chassis for rotatably driving in tandem the left-hand wheels of said pairs of wheels, remote control means coupled to said first and second motive means for selectively controlling the operation thereof independently of each other, and position indicating means carried by said chassis and responsive to movement of said chassis longitudinally of the pipe for producing an indication of the distance traveled.

17. The vehicle of claim 16, wherein said position indicating means includes a roller disposed in rolling engagement with the interior surface of the pipe, the rotation of said roller being directly proportional to the linear distance travelled by said chassis.

18. The vehicle of claim 17, and further including bias means resiliently urging said roller into rolling engagement with the pipe.

19. The vehicle of claim 17, and further including a star wheel mounted coaxially with said roller and having a plurality of equiangularly spaced-apart lugs, and sensor means sensing the passage of each of said lugs for producing a pulsating output signal.

20. The vehicle of claim 19, wherein said lugs are formed of a magnetically permeable material, said sensor means comprising a magnetic proximity sensor.

* * * * *